(12) United States Patent
Janssen et al.

(10) Patent No.: US 6,225,254 B1
(45) Date of Patent: May 1, 2001

(54) MAINTAINING ACID CATALYST SITES IN SAPO MOLECULAR SIEVES

(75) Inventors: Marcel J. G. Janssen, Kessel-Lo; Machteld M. Mertens, Boortmeerbeek; Cornelius W. M. Van Oorschot, Brasschaat, all of (BE); Stephen N. Vaughn, Kingwood, TX (US); Hsiang-Ning Sun, Houston, TX (US); David R. Lumgair, Kingwood, TX (US)

(73) Assignee: Exxon Mobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/392,981

(22) Filed: Sep. 9, 1999

Related U.S. Application Data (60) Provisional application No. 60/137,931, filed on Jun. 7, 1999.

(51) Int. Cl.[7] ................................... B01J 27/182
(52) U.S. Cl. ........................... 502/214; 502/208
(58) Field of Search ..................... 502/208, 214

(56) References Cited

U.S. PATENT DOCUMENTS

| | | | |
|---|---|---|---|
| 4,440,871 | 4/1984 | Lok et al. | 502/214 |
| 4,499,327 | 2/1985 | Kaiser | 585/640 |
| 4,677,242 | 6/1987 | Kaiser | 585/638 |
| 4,677,243 | 6/1987 | Kaiser | 585/638 |
| 4,752,651 | 6/1988 | Kaiser | 585/640 |
| 4,861,938 | 8/1989 | Lewis et al. | 585/640 |
| 5,095,163 | 3/1992 | Barger | 585/640 |
| 5,185,310 * | 2/1993 | Degnan et al. | 502/214 |
| 5,191,141 | 3/1993 | Barger et al. | 585/640 |
| 5,248,647 * | 9/1993 | Barger | 502/214 |
| 5,264,203 | 11/1993 | Beck et al. | 423/703 |
| 5,714,662 | 2/1998 | Vora et al. | 585/640 |
| 5,714,663 | 2/1998 | Serrand et al. | 585/648 |

OTHER PUBLICATIONS

Dumont et al., Xe–NMR Investigation of SAPO–37, Applied Catalysis, vol. 54, pp. I1–16, 1989.*

Pires et al., Silicoaluminophosphate Molecular Sieves, React. Kinet. Catal. Lett., vol. 43, No. 2, pp. 313–319, 1991.*

Khouzami et al., Structural, Acidic and Catalytic Properties of SAPO–11 Molecular Sieves, Innovation in Zeolite Materials Science.*

Methanol Conversion to Light Olefins (Clarence D. Chang) (1984) no month.

Production of Chemicals from Methanol (Warren W. Kaeding & Stephen A. Butter) (1980) no month.

Converting Natural Gas to Ethylene and Propylene by the UOP/Hydro MTO Process (Barger et al.) (12th International Zeolite Conference, 1999 Materials Research Society) no month.

Synthesis and Properties of SAPO–37 (Adeola F. Ojo et al.) 1991 no month.

Synthesis and Properties of SAPO–5 Molecular Sieves, Silicon Incorporation into the Framework (Adeola F. Ojo et al.) 1992 no month.

The effect of crystallite size on the activity and selectivity of the reaction of ethanol and 2–propanol over SAPO–34, Dahl et al., Microporous and Mesoporous Materials 29 (1999) pp. 159–171 no month.

* cited by examiner

*Primary Examiner*—Elizabeth D. Wood
(74) *Attorney, Agent, or Firm*—Bradley A. Keller (57) ABSTRACT

This invention is directed to a molecular sieve having acid catalyst sites and a method of maintaining the acid catalyst sites of a template-containing silicoaluminophosphate molecular sieve. The method comprises providing a template-containing silicoaluminophosphate molecular sieve and heating the molecular sieve in an oxygen depleted environment under conditions effective to maintain or preserve the number of acid catalyst sites. The heated molecular sieve exhibits at least one peak in the infrared region in a range of from 3630 $cm^{-1}$ to 3580 $cm^{-1}$. Preferably, the heated molecular sieve exhibits a combined peak area in the 3630 $cm^{-1}$ to 3580 $cm^{-1}$ range of at least 10% of a total peak area of all peaks in an infrared region between 4000 $cm^{-1}$ to 3400 $cm^{-1}$.

26 Claims, 2 Drawing Sheets

MAINTAINING ACID CATALYST SITES IN SAPO MOLECULAR SIEVES

This application claims priority to U.S. Provisional Patent Application No. 60/137,931, filed Jun. 7, 1999, the entire disclosure of which is incorporated herein by reference.

FIELD OF THE INVENTION

This invention relates to a method of maintaining acid catalyst sites of a silicoaluminophosphate (SAPO) molecular sieve. The molecular sieve can be used to make an olefin product by contacting the activated molecular sieve with an oxygenate feedstock. Preferred oxygenate feedstocks are alcohols and ethers, and the olefin product desirably contains high concentrations of ethylene and propylene. The invention also relates to a SAPO molecular sieve which exhibits at least one peak in a specific IR spectrum.

BACKGROUND OF THE INVENTION

Silicoaluminophosphates (SAPOs) have been used as absorbents and catalysts. As catalysts, SAPOs have been used in processes such as fluid catalytic cracking, hydrocracking, isomerization, oligomerization, the conversion of alcohols or ethers, and the alkylation of aromatics. To be useful as a catalysts, SAPO molecular sieves have to be activated. Methods of activating SAPOs are known.

U.S. Pat. No. 4,681,864 to Edwards et al. discuss the use of SAPO-37 molecular sieve as a commercial cracking catalyst. It is disclosed that activated SAPO-37 molecular sieve has poor stability. However, stability can be improved by using a particular activation process. According to the process, organic template is removed from the core structure of the sieve just prior to contacting with feed to be cracked. The process calls for subjecting the sieve to a temperature of 400–800° C. within the catalytic cracking unit.

U.S. Pat. No. 5,185,310 to Degnan et al. discloses another method of activating silicoaluminophosphate molecular sieve compositions. The method calls for contacting a crystalline silicoaluminophosphate with gel alumina and water, and thereafter heating the mixture to at least 425° C. The heating process is first carried out in the presence of an oxygen depleted gas, and then in the presence of an oxidizing gas. The object of the heating process is to enhance the acid activity of the catalyst. The acid activity is enhanced as a result of the intimate contact between the alumina and the sieve.

Briend et al., *J.Phys. Chem.* 1995, 99, 8270–8276, teach that SAPO-34 loses its crystallinity when the template has been removed from the sieve and the de-templated, activated sieve has been exposed to air. Data is presented, however, which suggest that over at least the short term, crystallinity loss is reversible. Even over a period of a couple years, the data suggest that crystallinity loss is reversible when certain templates are used.

As seen from the disclosure herein, we have found that SAPO molecular sieves will exhibit a shortened catalytic life when the catalytic sites are activated and exposed to a moisture-containing environment. This loss of catalytic life is likely not reversible, and can occur over a very short period of time. In essence, this loss of catalytic life is due to a loss in the number of acid catalytic sites. It is desirable, therefore, to obtain a SAPO molecular sieve that can be activated with little to no loss in acid catalyst sites, and exhibit a relatively long catalytic life. Such a molecular sieve would be highly desirable for use in a wide variety of catalytic compositions, which could be used in a variety of catalytic processes.

SUMMARY OF THE INVENTION

In order to overcome at least one of the many problems inherent in the prior art, the invention provides a method of maintaining acid catalyst sites of a silicoaluminophosphate (SAPO) molecular sieve. SAPO molecular sieves are compositions which act as catalysts in converting various hydrocarbon feeds to products. The compositions are manufactured by reacting a mixture of several chemical components. One of the components used in the reaction process is a template, although more than one template can be used. The templates are used to form channels or tunnel like structures (also called microporous structure) within the SAPO composition. To activate the SAPO composition so that it can be used as a catalyst, the template must be removed. These leaves behind an open microporous structure in which feedstock can enter, contact the catalytic sites, and the resulting product can exit. The manner in which the template is removed will affect the acid catalyst sites that are within the microporous structure.

In order to preserve catalytic activity, i.e., maintain acid catalyst sites, this invention provides a method which comprises providing a template-containing silicoaluminophosphate molecular sieve and heating the template-containing silicoaluminophosphate molecular sieve in an oxygen depleted environment under conditions effective to provide an integrated catalyst life that is greater than that obtained in a non-oxygen depleted environment. The heated molecular sieve exhibits at least one peak in the infrared region in a range of from 3630 cm$^{-1}$ to 3580 cm$^{-1}$. Preferably, the heated molecular sieve exhibits a combined peak area in the 3630 cm$^{-1}$ to 3580 cm$^{-1}$ range of at least 10% of a total peak area of all peaks in an infrared region between 4000 cm$^{-1}$ to 3400 cm$^{-1}$.

In a preferred embodiment, the activated molecular sieve can be used to make an olefin product from an oxygenate feedstock. This method comprises providing an activated molecular sieve exhibiting a total peak area in an infrared region from 3630 cm$^{-1}$ to 3580 cm$^{-1}$ that is at least 10% of a total peak area in an infrared region from 4000 cm$^{-1}$ to 3400 cm$^{-1}$, and contacting the activated molecular sieve with the oxygenate feedstock under conditions effective to convert the oxygenate feedstock to an olefin product. The olefin product made according to this method is also included as part of the invention. In addition, the invention includes a polyolefin made by contacting the olefin product with a polyolefin-forming catalyst under conditions effective to convert the olefin to polyolefin.

The molecular sieve is preferably selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAP-40, SAPO-41, SAPO-42, SAPO-44, SAPO-47, and SAPO-56, metal containing forms thereof, and mixtures thereof. More preferably, the molecular sieve is selected from the group consisting of SAPO-18, SAPO-34, SAPO-35, SAPO-44, SAPO-47, metal containing forms thereof, and mixtures thereof.

In another preferred embodiment the heated molecular sieve exhibits an integrated catalyst life of at least 4 grams of methanol converted per gram of molecular sieve. It is also preferred that the molecular sieve have a pore size of less than 5 angstroms.

In the method, it is preferred that heating be carried out in an oxygen depleted environment. Preferably, the oxygen depleted environment is substantially free of $O_2$. More preferably, the oxygen depleted environment has an oxygen partial pressure of less than about 1.0 psia, more preferably less than about 0.2 psia.

The molecular sieve is heated under conditions sufficient to remove substantially all of the template from the molecular sieve. Preferably, the molecular sieve is heated to a temperature of 200 to 800° C. The molecular sieve is preferably heated substantially in the absence of oxygen.

In yet another preferred embodiment, the template is selected from the group consisting of a tetraethyl ammonium salt, cyclopentylamine, aminomethyl cyclohexane, piperidine, triethylamine, cyclohexylamine, tri-ethyl hydroxyethylamine, morpholine, dipropylamine, pyridine, isopropylamine and mixtures thereof.

DESCRIPTION OF THE DRAWINGS

The invention will be better understood by reference to the Detailed Description of the Invention when taken together with the attached drawings, wherein.

DETAILED DESCRIPTION OF THE INVENTION

Silicoaluminophosphate (SAPO) molecular sieves are compositions which act as catalysts in converting various hydrocarbon feeds to products. These compositions are particularly suitable for converting oxygenate type feedstocks (e.g., alcohols and ethers) to products containing a relatively high degree of olefins (e.g. molecules having at least one non-saturated hydrocarbon bond), along with a variety of other hydrocarbon compositions.

SAPOs are manufactured by reacting a mixture of several chemical components. One of the components used in the reaction process is a template, although more than one template can be used. Templates are typically referred to as structure directing agents, and typically contain nitrogen, phosphorus, oxygen, carbon, hydrogen or some combination thereof. They are used to form channels or tunnel like structures (also called microporous structure) within the SAPO composition. For the SAPO materials to be useful as catalyst compositions, however, the template must be removed to open up the channels or tunnel-like structures. This allows feedstocks to flow into the channels and contact catalytic sites located within the channels, as long as the feedstock components are not too large to enter the microporous structure. Thus, the SAPO material is actually a molecular sieve, acting to sieve or screen out large molecules from contacting catalytic sites within the pores. Products which are formed by contacting feed with catalyst sites can then flow out of any one of the numerous pores within the SAPO composition, as long as nothing is blocking its path or as long as the initial product does not keep reacting and become too large to escape.

It is known that once the template material is removed from the SAPO composition, the remaining pore structure is sensitive to moisture. Briend et al., supra, have indicated that this is a reversible process such that heating to remove moisture within the pores will result in recovery of the original pore structure.

What has not been previously demonstrated, however, is that the manner in which the template is removed has an effect on the catalytic life of the SAPO material. Proper removal of the template actually minimizes the loss of the acid catalyst sites within the pore structure. This minimizes the loss of catalytic activity without changing the chemical make up of the SAPO material.

The silicoaluminophosphate molecular sieves of this invention comprise a three-dimensional microporous crystal framework structure of $[SiO_2]$, $[AlO_2]$ and $[PO_2]$ tetrahedral units. The sieves also exhibit a particularly desirable Broensted acid OH group spectrum, when the template material has been properly removed.

Broensted acid OH groups can be conveniently characterized by Diffused Reflectance Infrared (DR IR) spectroscopy. The groups can be found throughout a range of 4000 $cm^{-1}$ to 3400 $cm^{-1}$ of the IR spectrum. However, silicoaluminophosphate molecular sieves which exhibit desirable catalytic activity upon appropriate template removal have Broensted acid OH groups having one or more bands in the IR with wave numbers ranging from about 3630 $cm^{-1}$ to about 3580 $cm^{-1}$, with non-Broensted OH groups like Al—OH, P—OH and/or Si—OH being largely located in the range of about 4000 $cm^{-1}$ to about 3630 $cm^{-1}$. The non-Broensted OH groups are also typically located on the external surface of the molecular sieve or at regions within the sieve which exhibit internal defects. Preferably, the SAPO molecular sieve exhibits one or more peaks in the infrared region in the range of 3630 $cm^{-1}$ to 3580 $cm^{-1}$ and have a combined peak area in that region of at least 10% of the total peak area of all peaks in the infrared region in the range between 4000 $cm^{-1}$ to 3400 $cm^{-1}$.

Silicoaluminophosphate molecular sieves are generally classified as being microporous materials having 8, 10, or 12 membered ring structures. These ring structures can have an average pore size ranging from about 3.5–15 angstroms. Preferred are the small pore SAPO molecular sieves having an average pore size ranging from about 3.5 to 5 angstroms, more preferably from 4.0 to 5.0 angstroms. These preferred pore sizes are typical of molecular sieves having 8 membered rings.

In general, silicoaluminophosphate molecular sieves comprise a molecular framework of corner-sharing $[SiO_2]$, $[AlO_2]$, and $[PO_2]$ tetrahedral units. This type of framework is effective in converting various oxygenates into olefin products. The $[PO_2]$ tetrahedral units within the framework structure of the molecular sieve of this invention can be provided by a variety of compositions. Examples of these phosphorus-containing compositions include phosphoric acid. organic phosphates such as triethyl phosphate, and aluminophosphates. The phosphorous-containing compositions are mixed with reactive silicon and aluminum-containing compositions under the appropriate conditions to form the molecular sieve.

The $[AlO_2]$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The $[SiO_2]$ tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a $[MeO_2]$ tetrahedral unit. The $[MeO_2]$ tetrahedral unit carries a net electric charge depending on the valence state of the metal substituent. When the metal component has a valence state of +2, +3, +4, +5, or +6, the net electric charge is between −2 and +3. Incorporation of the metal component is typically accomplished adding the metal component during synthesis of the molecular sieve. However, post-synthesis ion exchange can also be used.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAP-40, SAP-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

The silicoaluminophosphate molecular sieves are synthesized by hydrothermal crystallization methods generally known in the art. See, for example, U.S. Pat. Nos. 4,440,871; 4,861,743; 5,096,684; and 5,126,308, the methods of making of which are expressly incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100–250° C., until a crystalline product is formed. Formation of the crystalline product can take anywhere from around 2 hours to as much as 2 weeks. In some cases, stirring or seeding with crystalline material will facilitate the formation of the product.

Typically, the molecular sieve product will be formed in solution. It can be recovered from solution by standard means, such as by centrifugation or filtration. The product can also be washed, recovered by the same means and dried.

As a result of the crystallization process, the recovered sieve contains within its pores at least a portion of the template used in making the initial reaction mixture. The crystalline structure essentially wraps around the template, and the template must be removed to obtain catalytic activity. Once the template is removed, the crystalline structure that remains has what is typically called an intracrystalline pore system.

The reaction mixture can contain one or more templates. Templates are structure directing agents, and typically contain nitrogen, phosphorus, oxygen, carbon, hydrogen or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly directing than another.

Representative templates include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof. Preferred templates are triethylamine, cyclohexylamine, piperidine, pyridine, isopropylamine, tetraethyl ammonium salts, and mixtures thereof. The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Preferred tetraethyl ammonium salts are tetraethyl ammonium hydroxide and tetraethyl ammonium phosphate.

Conventionally template is removed from the molecular sieve material by a heat treatment process. For example, the template can be calcined, or essentially combusted, in the presence of an oxygen-containing gas, by contacting the template-containing sieve in the presence of the oxygen-containing gas and heating at temperatures from 200° C. to 800° C.

In this invention, however, the manner of removing the template has an impact upon the catalytic performance of the molecular sieve. Moreover, the procedure used can have a profound effect on the Broensted acid sites, as characterized by DR IR spectroscopy. Upon proper removal of the template, a material is obtained which has a much longer catalyst life, particularly in converting oxygenate to olefin, and the material is well defined in the IR region characteristic for Broensted acid sites.

According to the invention, a template-containing silicoaluminophosphate molecular sieve is heated in the presence of an oxygen depleted environment under conditions effective to substantially extend the catalytic life of the sieve. Under these conditions, the integrated catalyst life will be greater than that obtained when heating is performed at non-oxygen depleted levels. The oxygen depleted environment is one that has a substantially low oxygen partial pressure. Preferably, the oxygen partial pressure of the oxygen depleted gas environment will be less than about 1.0 psia, more preferably less than about 0.2 psia (corresponding to approximately 6.8 mol % oxygen and 1.4 mol % oxygen, respectively, at atmospheric pressure). The oxygen depleted environment can be provided by applying a vacuum sufficient to substantially lower the oxygen partial pressure. The oxygen depleted environment can also be provided by filling a reactor system with oxygen depleted gas using a diluent such as nitrogen, helium, hydrogen, xenon, argon, flue gas, or any combination thereof.

There will be little if any combustion of the template material in an oxygen depleted environment due to the lack of oxygen. Rather than combustion, which theoretically forms carbon dioxide, water, and possibly various contaminants, the template will, in general, break apart and leave the microporous structure of the SAPO material. The smaller and more volatile template components will leave much more readily than larger components. Because some template components may remain in the microporous structure, even after the complete heat treatment process in an oxygen depleted environment, it is preferred to subject the heat treated SAPO to a final calcination. In such an embodiment, it is particularly desirable to heat the SAPO molecular sieve in an oxygen depleted environment for 10–75% of the total heat treating time, preferably 15–60% of the total heat treating time. The total heat treating time means the total time that the molecular sieve is heat treated in an oxygen depleted and a non-oxygen depleted environment. The total combined heating time is preferably between 10 minutes and 24 hours.

The preferred temperature range for template removal in an oxygen depleted environment is between 200° C. and 800° C., more preferably between 500° C. and 750° C. The molecular sieve is heated until the template is sufficiently removed, preferably between 5 minutes and 24 hours.

Calcination to remove any remaining template can be performed according to conventional processes. These processes generally involve heat treating in an environment that contains oxygen at a partial pressure of greater than 1 psia, preferably greater than 2 psia. Various gases can be used to dilute the oxygen. Examples include nitrogen, helium, xenon, argon, flue gas, or any combination thereof. In a preferred embodiment, calcination is performed in non-oxygen depleted air. The non-oxygen depleted air can be partially diluted using any dilution gas, with nitrogen or flue gas being preferred.

The preferred temperature range for calcination is between 200° C. and 800° C., more preferably between 500° C. and 750° C. Calcination is continued until any remaining template is sufficiently removed, preferably between 5 minutes and 24 hours. At the end of calcination, carbon on catalyst is preferably below 0.5 wt %, preferably below 0.2 wt %, most preferably below 0.1 w %.

In a preferred embodiment, oxygen partial pressure can be adjusted according to the amount of template in the microporous structure. In general, the less template occupying the microporous structure, the greater the oxygen partial pressure can be during heating. In a most preferred form, a gas and a SAPO molecular sieve are flowed into a contact system and contacted with one another in a countercurrent direction. The gas coming into the system preferably contains oxygen at a partial pressure of greater than 1 psia, preferably greater than 2 psia. As the gas moves in countercurrent contact with the molecular sieve, the oxygen in the gas will combust template remaining in the microporous structure. This means that as the gas moves through the contact system, it will become depleted as a result of the combustion process. If the system is appropriately sized, the gas coming into contact with molecular sieve entering the contact system will be oxygen depleted. The countercurrent contact process is preferably conducted such that the SAPO molecular sieve is in an oxygen depleted environment for 10–75% of the total heat treating time in the contact system, preferably 15–60% of the total heat treating time in the contact system.

In another preferred embodiment, the gas supplied to the calcination process comprises oxygen in an amount that is less than that required in a standard combustion reation of template. This means that the quantity should be calculated based on theoretical complete combustion of template to form carbon dioxide and water as the main combustion products.

In the countercurrent contact process, it is preferred to recycle the gas exiting the contact system so that it can be reused as a dilution gas. Dilution gas, whether recycle or make-up, is preferably input into the countercurrent contact system such that the gas entering the contact system contains oxygen at a substoichiometric amount for complete combustion reaction. This will ensure that molecular sieve entering the contact system will contact gas that is sufficiently oxygen depleted.

The gas exiting the countercurrent contact system is likely to be high in partially decomposed template. The decomposed template will be present as a result of the heat treatment in the oxygen depleted environment. Therefore, it is preferred to burn off or combust the exit gas prior to recycle.

A silicoaluminophosphate molecular sieve in which the template has been properly removed exhibits one or more peaks in the infrared region in the range of 3630 cm$^{-1}$ to 3580 cm$^{-1}$. Preferably, the molecular sieve has a combined peak area in the 3630 cm$^{-1}$ to 3580 cm$^{-1}$ range of at least 10% of the total peak area of all peaks in the infrared region in the range between 4000 cm$^{-1}$ to 3400 cm$^{-1}$.

A molecular sieve or a catalyst containing the molecular sieve will exhibit minimal loss or maintain a maximum level of acid catalyst sites when the template has been properly removed. Maintenance of acid catalyst sites is obtained when a template-containing silicoaluminophosphate molecular sieve is heated in an oxygen depleted environment under conditions effective to provide an integrated catalyst life that is greater than that obtained in a non-oxygen depleted environment.

Integrated catalyst life is defined herein as the total weight of methanol converted per weight of silicoaluminophosphate molecular sieve at the end of a run. If a catalyst containing a silicoaluminophosphate molecular sieve is evaluated, only the weight of silicoaluminophosphate molecular sieve in the catalyst is used in the calculation of the integrated catalyst life. The end of the run is the point in time when methanol conversion is less than 10 wt %. The conditions of the run should be kept relatively constant. For the purposes of calculating integrated catalyst life, each run should be made using a standard ½" diameter SS, fixed bed reactor at 450° C., and using 100% methanol as the feed at a reactor pressure of 25 psig (i.e., a methanol partial pressure of 25 psig). Although it is possible for the binder or any other catalyst component to adversely affect the integrated catalyst life of the molecular sieve itself, the effects should be such that the impact is minimal, and that the integrated catalyst life of the catalyst still be within the preferred parameters.

The integrated catalyst life is calculated as:

$$\sum_i WHSV * C_i * (t_i - t_{(i-1)})/60$$

where
WHSV=weight hourly space velocity, based on SAPO molecular sieve content of the catalyst (units=hr$^{-1}$);
$C_i$=the weight fraction of methanol conversion at time on stream $t_i$; and
$t_i$=time on stream i in minutes (units=min.).
WHSV is defined in the calculation of integrated catalyst life as the weight of the feed fed to the ½" reactor over time (per hour) divided by the weight of the silicoaluminophosphate molecular sieve component of the catalyst in the reactor. The silicoaluminophosphate molecular sieve component of the catalyst is intended to mean only the silicoaluminophosphate molecular sieve portion that is contained within the catalyst. This excludes catalyst components such as nonsilicoaluminophosphate molecular sieves, binders, diluents, inerts, rare earth components, etc. The preferred integrated catalyst life will be at least 4 grams of methanol converted per gram of the silicoaluminophosphate molecular sieve.

Methanol conversion can be measured using a reactor equipped with an on-line gas chromatograph (GC) for product analysis. At various times on stream, $t_i$, samples are withdrawn from the product stream and are analyzed.

The silicoaluminophosphate molecular sieves may be admixed (blended) with other materials. When blended, the resulting composition is typically referred to as a silicoaluminophosphate (SAPO) catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, other non-zeolite catalyst components, zeolite catalyst components, alumina or alumina sol, titania, zirconia, quartz, silica or silica or silica sol, and mixtures thereof. These components are also effective in reducing overall catalyst cost, acting as a thermal sink to assist in heat shielding the catalyst during regeneration, densifying the catalyst and increasing catalyst strength. When blended with non-silicoaluminophosphate molecular sieve materials, the amount of molecular sieve which is contained in the final catalyst product ranges from 10 to 90 weight percent of the total catalyst, preferably 30 to 70 weight percent of the total catalyst.

A silicoaluminophosphate catalyst, which comprises the molecular sieve, binder, and any other catalyst or inert component, may or may not exhibit the exact same infrared spectrum as the silicoaluminophosphate molecular sieve by itself. This is because the binder and other catalyst components may have some effect on the infrared analysis of the finished catalyst. Even if there should be some distortion in the finished catalyst of the infrared characterization of the molecular sieve due to the presence of binder and other catalyst or inert components, the method of maintaining the acid catalyst sites of the molecular sieve composition described herein will provide a finished catalyst composition that has the catalytic benefits associated with the molecular sieve itself.

In this invention, a feed containing an oxygenate is contacted in a reaction zone of a reactor apparatus with a molecular sieve catalyst at process conditions effective to produce light olefins, i.e., an effective temperature, pressure, WHSV (weight hour space velocity) and, optionally, an effective amount of diluent, correlated to produce light olefins. Usually, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

Olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of product. An operating temperature of at least 300° C., and up to 500° C. is preferred.

Owing to the nature of the process, it may be desirable to carry out the process of the present invention by use of the molecular sieve catalysts in a dynamic bed system or any system of a variety of transport beds rather than in a fixed bed system. The critical feature of the reactor system utilized is the ability to operate at high space velocities.

The conversion of oxygenates to produce light olefins may be carried out in a variety of catalytic reactors, including, but not limited to, fluid bed reactors and concurrent riser reactors as described in "Free Fall Reactor," *Fluidization Engineering,* D. Kunii and O. Levenspiel, Robert E. Krieger Publishing Co. NY, 1977, incorporated in its entirety herein by reference. Additionally, countercurrent free fall reactors may be used in the conversion process. See, for example, U.S. Pat. No. 4,068,136 and "Riser Reactor", *Fluidization and Fluid-Particle Systems,* pages 48–59, F. A. Zenz and D. F. Othmo, Reinhold Publishing Corp., NY 1960, the descriptions of which are expressly incorporated herein by reference.

Any standard commercial scale reactor system can be used, including fixed bed or moving bed systems. The commercial scale reactor systems can be operated at a weight hourly space velocity (WHSV) of from 1 hr$^{-1}$ to 1000 hr$^{-1}$. In the case of commercial scale reactors, WHSV is defined as the weight of hydrocarbon in the feed per hour per weight of silicoaluminophosphate molecular sieve content of the catalyst. The hydrocarbon content will be oxygenate and any hydrocarbon which may optionally be combined with the oxygenate. The silicoaluminophosphate molecular sieve content is intended to mean only the silicoaluminophosphate molecular sieve portion that is contained within the catalyst. This excludes components such as binders, diluents, inerts, rare earth components, etc.

Preferred reactors are co-current riser reactors and short contact time countercurrent free-fall reactors. In these preferred reactors, an oxygenate feedstock is preferably contacted with a molecular sieve catalyst at a WHSV of at least about 20 hr$^{-1}$, preferably in the range of from about 20 hr$^{-1}$ to 1000 hr$^{-1}$, and most preferably in the range of from about 20 hr$^{-1}$ to 500 hr$^{-1}$.

It is highly desirable to operate at a temperature of at least 300° C. and a Temperature Corrected Normalized Methane Sensitivity (TCNMS) of less than about 0.016, preferably less than about 0.012, more preferably less than about 0.01. It is particularly preferred that the reaction conditions for making olefin from oxygenate comprise a WHSV of at least about 20 hr$^{-1}$ producing olefins and a TCNMS of less than about 0.016.

As used herein, TCNMS is defined as the Normalized Methane Selectivity (NMS) when the temperature is less than 400° C. The NMS is defined as the methane product yield divided by the ethylene product yield wherein each yield is measured on, or is converted to, a weight % basis. When the temperature is 400° C. or greater, the TCNMS is defined by the following equation, in which T is the average temperature within the reactor in ° C.:

$$TCNMS = \frac{NMS}{1 + (((T - 400)/400) \times 14.84)}$$

The pressure also may vary over a wide range, including autogenous pressures. Effective pressures may be in, but are not necessarily limited to, pressures of from about 0.1 kPa to about 4 MPa. Preferred pressures are in the range of about 6.9 kPa to about 2 MPa, with the most preferred range being of from about 48 kPa to about 0.34 MPa. The foregoing pressures are exclusive of any oxygen depleted diluent, and thus, refer to the partial pressure of the oxygenate compounds and/or mixtures thereof with feedstock. At the lower and upper end of the foregoing pressure ranges, the rate of selectivity, conversion and/or reaction may not be optimum.

One or more oxygen depleted diluents may be present in the feedstock, for example, in an amount of from 1 to 99 molar percent, based on the total number of moles of all feed and diluent components fed to the reaction zone (or catalyst). Typical diluents include, but are not necessarily limited to helium, argon, nitrogen, carbon monoxide, carbon dioxide, hydrogen, water, paraffins, alkanes (especially methane, ethane, and propane), alkylenes, aromatic compounds, and mixtures thereof The preferred diluents are water and nitrogen. Water can be injected in either liquid or vapor form.

The process may be carried out in a batch, semi-continuous or continuous fashion. The process can be conducted in a single reaction zone or a number of reaction zones arranged in series or in parallel.

The level of conversion of the oxygenates can be maintained to reduce the level of unwanted by-products. Conversion can also be maintained sufficiently high to avoid the need for commercially unacceptable levels of recycling of unreacted feeds. A reduction in unwanted by-products is seen when conversion moves from 100 mol % to about 98 mol % or less. Recycling up to as much as about 50 mol % of the feed is commercially acceptable. Therefore, conversion levels which achieve both goals are from about 50 mol % to about 98 mol % and, desirably, from about 85 mol % to about 98 mol %. However, it is also acceptable to achieve conversion between 98 mol % and 100 mol % in order to simplify the recycling process. Oxygenate conversion may be maintained at this level using a number of methods familiar to persons of ordinary skill in the art. Examples include, but are not necessarily limited to, adjusting one or more of the following: the reaction temperature; pressure; flow rate (i.e., WHSV); level and degree of catalyst regeneration; amount of catalyst re-circulation; the specific reactor configuration; the feed composition; and other parameters which affect the conversion.

If regeneration is required, the molecular sieve catalyst can be continuously introduced to a regeneration zone where it can be regenerated, such as for example by removing carbonaceous materials or by oxidation in an oxygen containing atmosphere. In a preferred embodiment, the catalyst is subject to a regeneration step by burning off carbonaceous deposits accumulated during the conversion reactions.

The oxygenate feedstock comprises at least one organic compound which contains at least one oxygen atom, such as aliphatic alcohols, ethers, carbonyl compounds (aldehydes, ketones, carboxylic acids, carbonates, esters and the like), and the feedstock may optionally contain at least one compound containing a halide, mercaptan, sulfide, or amine, as long as the optional components do not significantly impede the performance of the catalyst. When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols, their unsaturated counterparts and the nitrogen, halogen and sulfur analogues of such. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

The method of making the preferred olefin product in this invention can include the additional step of making these compositions from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidization.

One skilled in the art will also appreciate that the olefins produced by the oxygenate-to-olefin conversion reaction of the present invention can be polymerized to form polyolefins, particularly polyethylene and polypropylene.

Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305, 538; 3,364,190; 5,892,079; 4,659,685; 4,076,698; 3,645, 992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred olefin-forming catalyst is a metallocene catalyst. The preferred temperature range of operation is between 50 and 240° C. and the reaction can be carried out at low, medium or high pressure. For processes carried out in solution, an inert diluent can be used, and the preferred operating pressure range is between 10 and 150 bars, with a preferred temperature range of between 120 and 230° C. For gas phase processes, it is preferred that the temperature generally be within a range of 60 to 160° C., and that the operating pressure be between 5 and 50 bars.

This invention will be better understood with reference to the following examples, which are intended to illustrate specific embodiments within the overall scope of the invention as claimed.

EXAMPLE 1

A sample of SAPO-34 having a DPA/TEAOH template was heated from ambient conditions to a temperature of about 525° C. at a rate of about 1° C. per minute, then cooled to ambient conditions in a closed oven. The procedure was performed in a shallow bed, injecting air at a rate of about 4.2 liters air/min.

EXAMPLE 2

A sample of SAPO-34 having a DPA/TEAOH template was heated from ambient conditions to a temperature of about 650° C. at a rate of about 10° C. per minute, then cooled to ambient conditions in situ in an IR spectrometer using a high temperature diffuse reflectance IR cell under vacuum at about 0.1 bar.

EXAMPLE 3

A sample of SAPO-34 having a DPA/TEAOH template was heated from ambient conditions to a temperature of about 650° C. at a rate of about 10° C. per minute, then cooled to ambient conditions in situ in an IR spectrometer using a high temperature diffuse reflectance IR cell under vacuum at about $6 \times 10^{-4}$ mbar.

EXAMPLE 4

Figure 1:
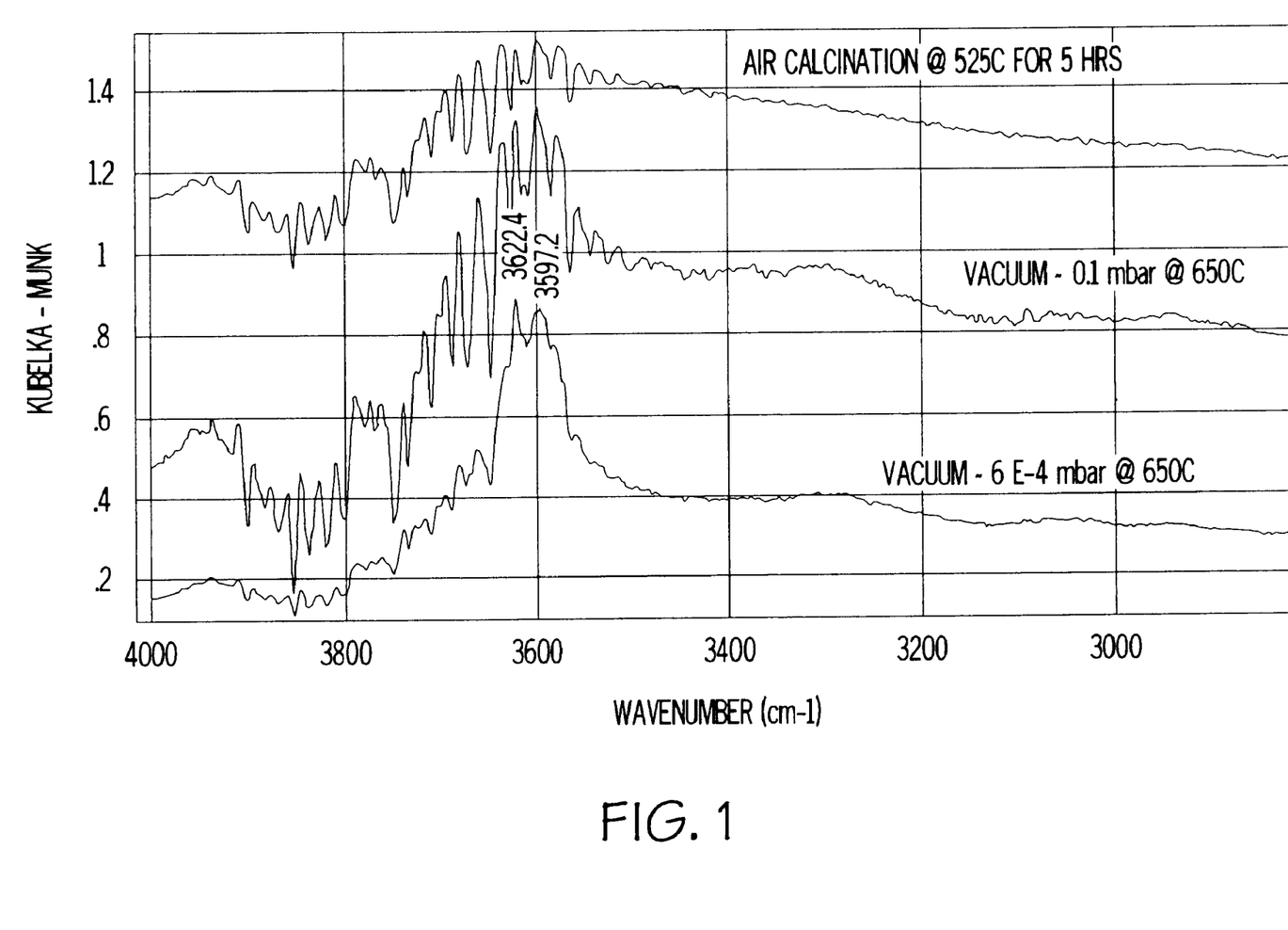
FIG. 1 shows the IR spectra in Broensted OH region of a SAPO-34 molecular sieve made with a TEAOH/DPA template as a function of activation procedure.

The products of Examples 1–3 were characterized by IR absorption using diffuse reflectance spectroscopy. The IR spectra were obtained, and are shown in FIG. 1. The IR spectra indicate that the Broensted acid characteristics of the SAPO material are affected according to the conditions upon which the template is removed.

EXAMPLE 5

Figure 2:
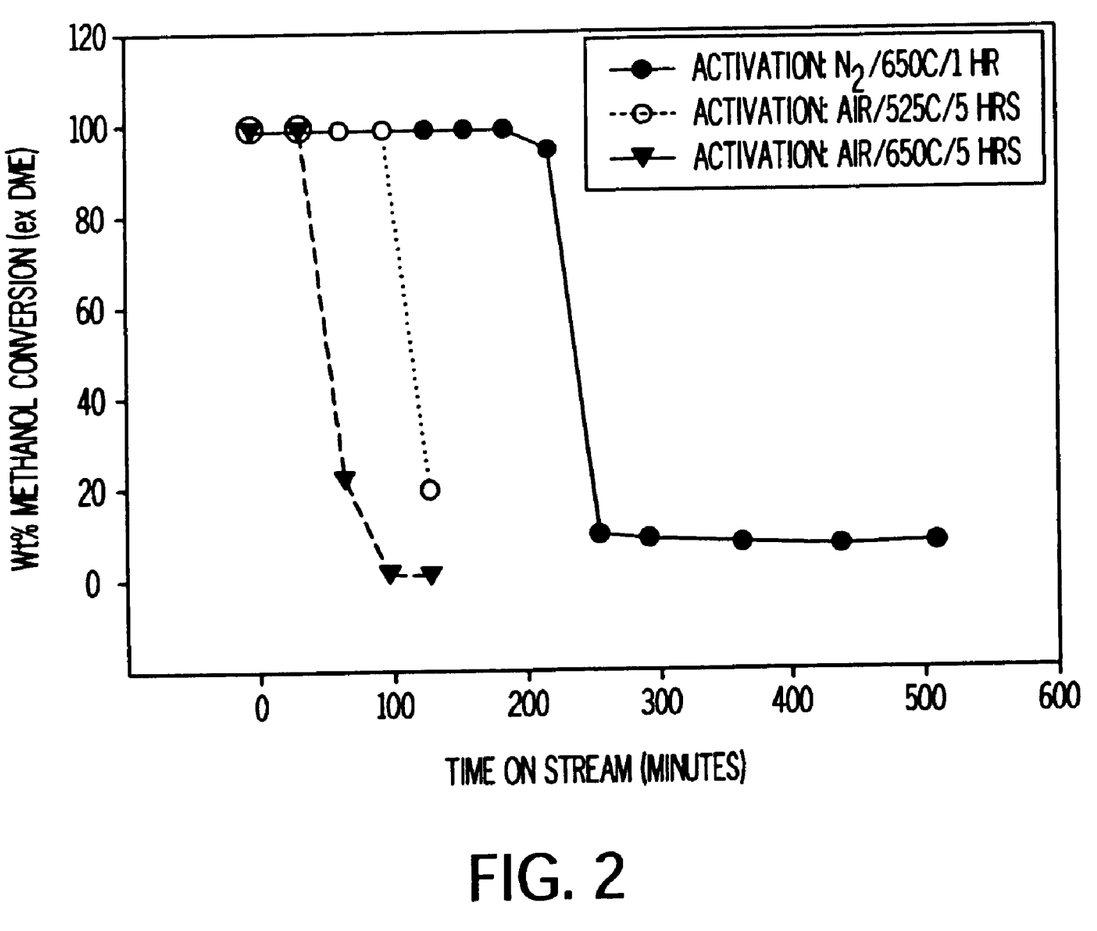
FIG. 2 shows a comparison of the catalyst life of a SAPO-34 molecular sieve made with a TEAOH/DPA template as a function of activation procedure.

A sample of SAPO-34 having a DPA/TEAOH template was heated in situ (i.e., in a fixed bed, continuous reactor) under nitrogen (50 ml/min) from ambient conditions to a temperature of about 650° C. at a rate of about 10° C. per minute; held for about 1 hour; then cooled to 450° C. and tested from methanol conversion. Methanol was fed to the reactor at a WHSV of 1.6 $hr^{-1}$ and a pressure of 0.3 barg. The reactor effluent was analyzed by an on-line GC. Methanol conversion was calculated as (100 - (wt % methanol left in product)). The result is shown in FIG. 2.

EXAMPLE 6

A sample of SAPO-34 having a DPA/TEAOH template was heated from ambient conditions to a temperature of about 525° C. at a rate of about 10° C. per minute; held for about 5 hours; then cooled to ambient conditions in a closed oven. The procedure was performed in a shallow bed, injecting air at a rate of about 4.2 liters air/min.

EXAMPLE 7

A sample of SAPO-34 having a DPA/TEAOH template was heated from ambient conditions to a temperature of about 650° C. at a rate of about 10° C. per minute; held for about 5 hours; then cooled to ambient conditions in a closed oven. The procedure was performed in a shallow bed, injecting air at a rate of about 4.2 liters air/min.

EXAMPLE 8

The products of Examples 1–7 were placed in separate ½" diameter SS reactors at 450° C. Methanol conversion was performed as in Example 5. The results are shown in FIG. 2.

EXAMPLE 9

Integrated catalyst life of the catalyst samples of Examples 5–7 was $$\sum_i WHSV * C_i * (t_i - t_{(i-1)})/60$$

calculated as
where
WHSV=weight hourly space velocity;
$C_i$=the wt % methanol conversion at time on stream $t_i$; and
$t_i$=time on stream i in minutes.

The integrated catalyst life of each catalyst sample is shown in Table 1.

TABLE 1

| Activation | Integrated Catalyst Life (gr. methanol/gr. mol. sieve) |
| --- | --- |
| $N_2$/650° C./1 hr. | 8.6 |
| air/525° C./5 hrs. | 3.7 |
| air/650° C./5 hrs. | 1.6 |

The data shown in FIG. 2 indicate that a significant improvement in catalyst life can be gained upon removal of the template in an oxygen depleted environment. In this case the oxygen depleted environment ($N_2$) is substantially free of $O_2$.

EXAMPLE 10

A catalyst composition comprising SAPO-34 molecular sieve is heat treated in a continuous rotary type calciner. Airflow is provided countercurrent to the direction of flow of the catalyst composition. The rate of airflow is provided at less than stoichiometric oxygen to template ratio (combustion basis to $CO_2$), which is approximately 600–1000 scc/min of air per g-of-catalyst fed/min, based on 13% hydrocarbon on catalyst. This ratio of volumetric airflow to catalyst feed rate can be adjusted for different hydrocarbon on catalyst. A diluent gas is mixed with the air to obtain the less than stoichiometric oxygen to template ratio. The amount of diluent gas is also sufficiently low to obtain a depleted oxygen environment for approximately ⅓ of the total calcination time. Total calcination time is the total amount of time the catalyst is in the calciner. In this example, total calcination time from 0.5–2 hr. Calcination temperature is approximately 650° C. for the bulk operation. At the completion of the process, the carbon on catalyst is less than 0.1 wt %. The calcined catalyst is placed in drums, and stored under a nitrogen blanket.

Having now fully described this invention, it will be appreciated by those skilled in the art that the invention can be performed within a wide range of parameters within what is claimed, without departing from the spirit and scope of the invention.

What is claimed is:

1. A method of maintaining acid catalyst sites of a silicoaluminophosphate molecular sieve comprising providing a template containing silicoaluminophosphate molecular sieve and heating the template containing silicoaluminophosphate molecular sieve in an oxygen depleted environment to provide an integrated catalyst life that is greater than that obtained in a non-oxygen depleted environment, the heated molecular sieve having a pore size of less than 5 angstroms.

2. The method of claim 1, wherein the heated molecular sieve exhibits at least one peak in the infrared region in a range of from 3630 $cm^{-1}$ to 3580 $cm^{-1}$.

3. The method of claim 2, wherein the heated molecular sieve exhibits a combined peak area in the 3630 $cm^{-1}$ range of at least 10% of a total peak area of all peaks in an infrared region between 4000 $cm^{-1}$ to 3400 $cm^{-1}$.

4. The method of claim 1, wherein the molecular sieve is selected from the group consisting of SAPO-18, SAPO-34, SAPO-35, SAPO44, SAPO-47, metal containing forms of each of the foregoing, and mixture thereof.

5. The method of claim 1, wherein the heated molecular sieve exhibits an integrated catalyst life of at least 4 grams of methanol converted per gram of molecular sieve.

6. The method of claim 1, wherein the oxygen depleted environment is substantially free of $O_2$.

7. The method of claim 1, wherein the oxygen depleted environment has an oxygen partial pressure of less than 1.0 psia.

8. The method of claim 1, wherein the oxygen depleted environment comprises a gas selected from the group consisting of nitrogen, helium, hydrogen, xenon, argon, and flue gas.

9. The method of claim 1, wherein the oxygen depleted environment is provided by applying a vacuum sufficient to substantially remove $O_2$.

10. The method of claim 1, wherein the molecular sieve is heated to a temperature of 200° C. to 800° C.

11. The method of claim 1, wherein the template is selected from the group consisting of a tetraethyl ammonium salt, cyclopentylamine, aminomethyl cyclohexane, piperidine, triethylamine, cyclohexylamine, tri-ethyl hydroxyethylamine, morpholine, dipropylamine, pyridine, isopropylamine and mixtures thereof.

12. The method of claim 1, wherein the molecular sieve is heated under conditions sufficient to remove substantially all of the template from the molecular sieve.

13. The method of claim 12, wherein the molecular sieve is heated substantially in the absence of oxygen.

14. A silicoaluminophosphate molecular sieve produced by the process comprising heating the silicoaluminophosphate molecular sieve to remove a template from within a crystalline microporous structure such that the heated silicoaluminophosphate molecular sieve exhibits a total peak area in an infrared region from $3630\ cm^{-1}$ to $3580\ cm^{-1}$ that is at least 10% of a total peak area in an infrared region from $4000\ cm^{-1}$ to $3400\ cm^{-1}$.

15. The silicoaluminophosphate molecular sieve of claim 14, wherein the molecular sieve is selected from the group consisting of SAPO-18, SAPO-34, SAPO-35, SAPO-44, SAPO-47, metal containing forms of each of the foregoing, and mixtures thereof.

16. A silicoaluminophosphate molecular sieve produced by the process comprising heating the silicoaluminophosphate molecular sieve in an oxygen depleted environment to remove a template from within a crystalline microporous structure such that the heated silicoaluminophosphate molecular sieve exhibits an integrated catalyst life of at least 4 grams of methanol converted per gram of molecular sieve, the heated molecular sieve having a pore size of less than 5 angstroms.

17. The silicoaluminophosphate molecular sieve of claim 16, wherein the sieve has a crystalline microporous structure and exhibits at least one peak in an infrared region in a range of from $3630\ cm^{-1}$ to $3580\ cm^{-1}$.

18. The silicoaluminophosphate molecular sieve of claim 17, wherein the heated molecular sieve exhibits a combined peak area in the $3630\ cm^{-1}$ to $3580\ cm^{-1}$ range of at least 10% of a total peak area of all peaks in an infrared region between $4000\ cm^{-1}$ to $3400\ cm^{-1}$.

19. The silicoaluminophosphate molecular sieve of claim 18, wherein the molecular sieve is selected from the group consisting of SAPO-18, SAPO-34, SAPO-35, SAPO-44, SAPO-47, metal containing forms thereof, and mixtures thereof.

20. The method of claim 3, wherein the heated molecular sieve exhibits a combined peak area in the $3630\ cm^{-1}$ to $3580\ cm^{-1}$ range of at least 20% of a total peak area of all peaks in an infrared region between $4000\ cm^{-1}$ to $3400\ cm^{-1}$.

21. The method of claim 20, wherein the heated molecular sieve exhibits a combined peak area in the $3630\ cm^{-1}$ to $3580\ cm^{-1}$ range of at least 30% of a total peak area of all peaks in an infrared region between $4000\ cm^{-1}$ to $3400\ cm^{-1}$.

22. The method of claim 1, wherein the heated molecular sieve exhibits a peak area ratio of 2:1, wherein the peak area ratio is defined as the peak areas between $3630\ cm^{-1}$ to $3580\ cm^{-1}$ and $4000\ cm^{-1}$ to $3850\ cm^{-1}$.

23. The method of claim 1, wherein the heated molecular sieve exhibits a peak area ratio of 4:1, wherein the peak area ratio is defined as the peak areas between $3630 cm^{-1}$ to $3580\ cm^{-1}$ and $3800\ cm^{-1}$ to $3750\ cm^{-1}$.

24. The method of claim 1, wherein heating the molecular sieve comprises heating in an oxygen depleted environment for 10% to 75% of the total heat treating time.

25. The method of claim 14, wherein heating the molecular sieve comprises heating in an oxygen depleted environment for 10% to 75% of the total heat treating time.

26. The method of claim 16, wherein heating the molecular sieve comprises heating in an oxygen depleted environment for 10% to 75% of the total heat treating time.

* * * * *